US008160894B2

(12) United States Patent
Osgood

(10) Patent No.: US 8,160,894 B2
(45) Date of Patent: Apr. 17, 2012

(54) SYSTEM AND METHOD FOR IMPROVING MEDICAL CARE

(76) Inventor: Kenneth Osgood, Las Vegas, NV (US)

( * ) Notice: Subject to any disclaimer, the term of this patent is extended or adjusted under 35 U.S.C. 154(b) by 1066 days.

(21) Appl. No.: 11/462,791

(22) Filed: Aug. 7, 2006

(65) Prior Publication Data

US 2008/0033760 A1    Feb. 7, 2008

(51) Int. Cl.
*G06Q 10/00* (2012.01)
*G06Q 50/10* (2012.01)
(52) U.S. Cl. ............................................. 705/2; 705/3
(58) Field of Classification Search .................. 705/2–3; 600/300
See application file for complete search history.

(56) References Cited

U.S. PATENT DOCUMENTS

| 2002/0188182 A1* | 12/2002 | Haines et al. ................. 600/300 |
| 2003/0074222 A1* | 4/2003 | Rosow et al. ..................... 705/2 |
| 2006/0206013 A1* | 9/2006 | Rothman et al. ............. 600/300 |

OTHER PUBLICATIONS

"How Should We Make the Admission Decision in Community Acquired Pneumonia?", Dominik Aronsky, MD and Nathan C. Dean, MD, Medical Clinics of North America, vol. 85, No. 6, Nov. 2001.*

* cited by examiner

*Primary Examiner* — Luke Gilligan
*Assistant Examiner* — Joseph Burgess
(74) *Attorney, Agent, or Firm* — Jeffrey D. Moy; Weiss & Moy, P.C.

(57) ABSTRACT

A computer system comprising a processor for executing program instructions and a memory coupled to the processor for storing the program instructions, the programming instructions comprising: enter intake data on a patient; entering symptoms the patient is experiencing and services performed on the patient, wherein all symptom and services listed in the program instructions are assigned a numeric number based on severity of the symptom and service; calculating total value of all numeric values of symptoms patient is experiencing and services performed on the patient; and making a recommendation to one of continue hospital stay or discharge of the patient.

19 Claims, 14 Drawing Sheets

Figure 7

SYSTEM AND METHOD FOR IMPROVING MEDICAL CARE

BACKGROUND OF THE INVENTION

1. Field of the Invention

The present invention relates to the medical industry and, more specifically, to a multi-functional medical software program that is used to support concurrent review hospital discharge or continued stay recommendations; to determine effective allocation of hospital staff and other resources; and to obtain data for quality improvement projects.

2. Description of the Prior Art

As healthcare cost increase throughout the world, healthcare providers must make difficult choices regarding how to provide the best possible services at prices their patients can afford. Although most clinicians would prefer to purchase every cutting edge medical technology available, they simply cannot afford to do so while still caring for their patients in an affordable manner.

One way to provide more efficient health care is to determine how and when a patient should be discharged. This particular area of health care has been the subject of numerous law suits which drive up the cost of health care. Determining whether a patient should remain hospitalized has traditionally been based on the subjective decision of a medical practitioner. The risks of a faulty decision not only have large economic repercussions to the health care provider, but literally affect the very life and well being of the patient. Because of this, many hospitalization stay decisions have been the source of bitter disputes and lawsuits between hospitals, insurance companies and the patients themselves.

To help avoid these disputes, several systems have been employed to provide an objective footing for hospital stay/discharge decision making. However these systems are complicated, hard to use, and sometimes yield ambiguous decisions.

Another way to provide more efficient health care is in the area of effective allocation of hospital staff and other medical resources. Many times, different areas in the hospital or medical center are either overstaffed or understaffed. These areas may further not have the proper resources to effectively diagnosis and treat patients. By effectively staffing all departments of the hospital, resources may be better utilized to better serve the patients and lower health care cost.

Therefore, it would be desirable to provide a system and method that overcomes the problems associated with the prior art. The system and method will provide a means for providing more efficient health care. The system and method will determine how and when a patient should be discharged. The system and method will further determine effective allocation of hospital staff and other resources. The system and method will further obtain data for quality improvement projects.

SUMMARY OF THE INVENTION

In accordance with one embodiment of the present invention, a computer system comprising a processor for executing program instructions and a memory coupled to the processor for storing the program instructions is disclosed. The programming instructions comprises: enter intake data on a patient; entering at least one of symptoms the patient is experiencing and services performed on the patient, wherein all symptom and services listed in the program instructions are assigned a numeric number based on severity of the symptom and service; calculating total value of all numeric values of symptoms patient is experiencing and services performed on the patient; and making a recommendation to one of continue hospital stay or discharge of the patient.

In accordance with another embodiment of the present invention, a computer system comprising a processor for executing program instructions and a memory coupled to the processor for storing the program instructions is disclosed. The programming instructions comprises: enter intake data on a patient; entering symptoms the patient is experiencing and services performed on the patient, wherein all symptom and services listed in the program instructions are assigned a numeric number based on severity of the symptom and service; calculating total value of all numeric values of symptoms patient is experiencing and services performed on the patient; making a recommendation to one of continue hospital stay or discharge of the patient; listing a plurality of different conditions/illnesses; displaying guidelines to show how to treat a selected condition/illness; entering marks for indicating that a particular measure has been taken to treat the selected condition/illness; monitoring resources consumed by all patients for one of a particular hospital, floor, and ward; and reviewing data to determine if one of the hospital, floor, ward has sufficient supplies and staffing.

The features, functions, and advantages can be achieved independently in various embodiments of the present invention or may be combined in yet other embodiments.

BRIEF DESCRIPTION OF THE DRAWINGS

The present invention will become more fully understood from the detailed description and the accompanying drawings, wherein:

FIG. 7 is a Symptoms/Services screen for Inpatient MAP module for the software application program;

DETAILED DESCRIPTION OF THE PREFERRED EMBODIMENT

Figure 1:
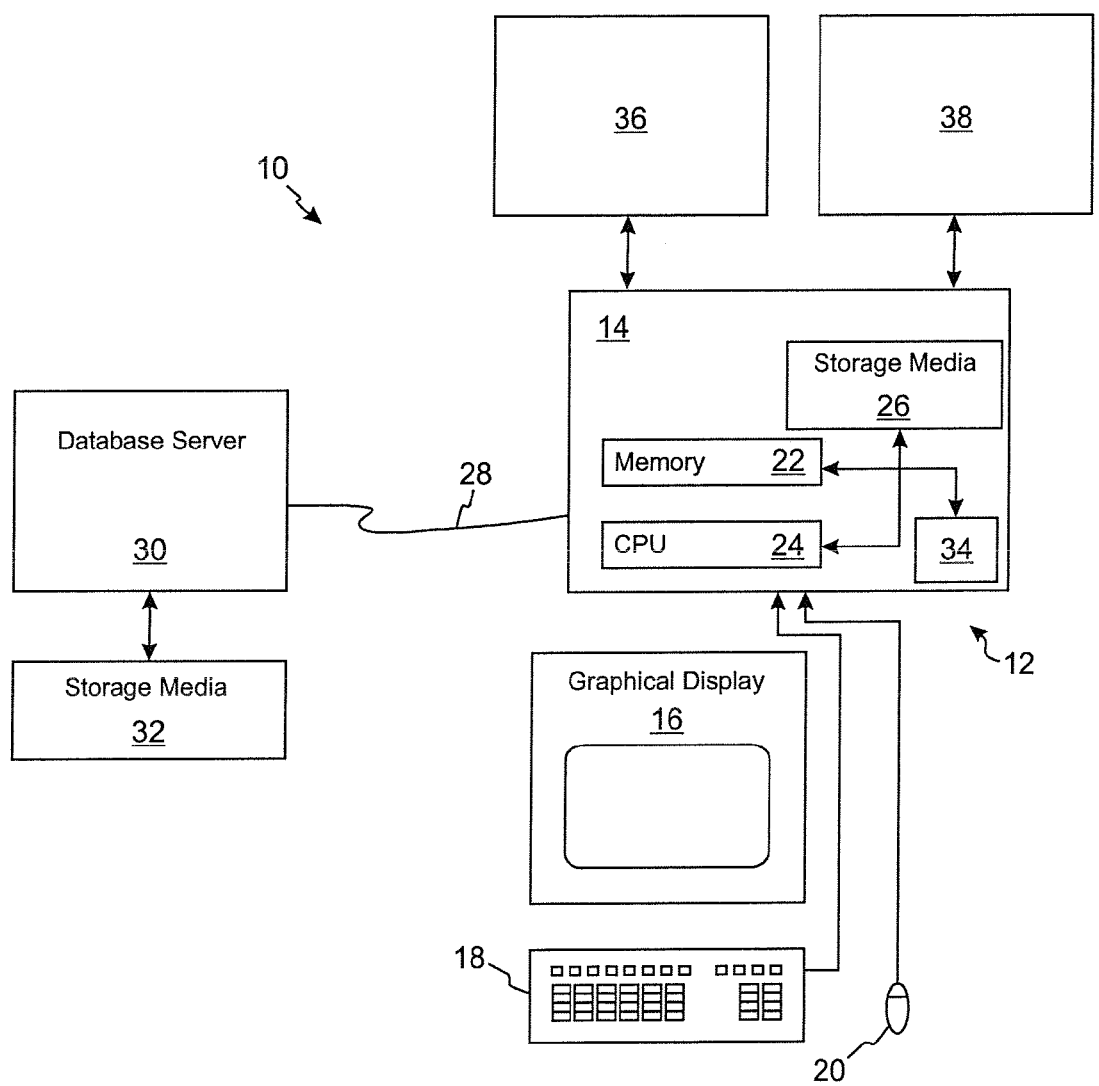
FIG. 1 is a is a simplified block diagram of a system for performing.

Referring to FIG. 1, a system 10 for providing more efficient health care is shown. The system 10 generally uses a main computer system 12. The computer system 12 will have a processor unit 14 and a display 16. Input devices are coupled to the processor unit 14. The input devices may be a keyboard 18, a mouse 20 and the like. Through the execution of program instructions forming a computer program product within the computer system 12, the computer system 12 will provide a means for providing more efficient health care. The computer system 10 will determine how and when a patient should be discharged. The computer system 12 will further determine effective allocation of hospital staff and other resources. The computer system 12 will further obtain data for quality improvement projects.

The program instructions may be located within a memory 22 of the processor unit 14 and executed by a central processing unit 24 (CPU). Any data stored from the running of the program instructions may be stored entirely within a storage media 26 and/or the memory 22.

Alternatively, the computer system 12 may have a connection 28 to a network such as a local-area network (LAN), wide-area network (WAN) or the Internet. The connection 28 may be a wired connection, a wireless connection, or the like. In a network implementation, the program instructions may be located within a database server 30. Any data stored may be stored in a storage media 32 coupled to the database server 30.

One or more outside computers 36 and 38 may be coupled to the main computer system 12 and/or the database server 30 via a connection. The connection may be via a local-area network (LAN), wide-area network (WAN) or the Internet. The connection may be a wired connection, a wireless connection, or the like. The outside computers 36 and 38 will have access to the main computer system 12 and/or the database server 30. The outside computers 36 and 38 will allow another party to input data into the main computer system 12 and/or the database server 30.

The computer program within the computer system 12 comprises three (3) modules: The Medical Scientific Resource Monitor to Assess Progress (MSR MAP) is used to support concurrent review hospital discharge or continued stay recommendations (Inpatient MAP); Resource Monitor to Assess Progress (Resource MAP) is used to determine effective allocation of hospital staff and other resources; and a Quality Monitor to Assess Progress (Quality MAP) is used to obtain data for quality improvement projects.

As stated above, the computer program is installed on the computer system 12. The computer system 12 may be a desktop computer system. However, the computer program may also be installed in a laptop, notepad, personal digital assistant (PDA), and the like to be portable and mobile.

The MSR MAP is a single user tool that uploads data into an enterprise-wide information system of unlimited users. It is an application which features use-intuitive data entry. The MSR Inpatient MAP is a concurrent review instrument completed by a nurse or physician reviewer, on site or telephonic. It is specifically designed for the daily review of hospitalized patients admitted to acute care hospitals or for extended observation. The reviewer uses the MSR inpatient MAP to support a discharge or continued inpatient or observation stay recommendation.

Figure 3:
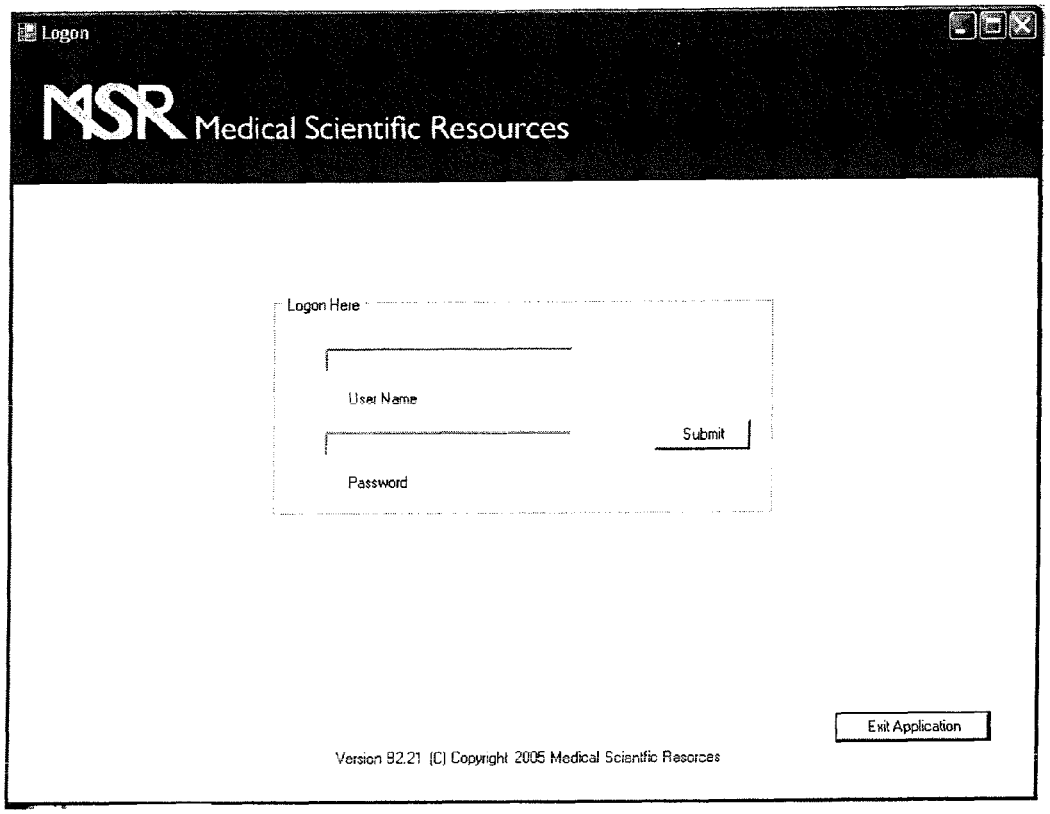
FIG. 3 is the logon screen for the software application program.

The computer program will generally have a secure access to prevent unauthorized users from entering and/or reviewing data. As shown in FIG. 3, to access the computer program, a person will have to log into the computer program. In accordance with one embodiment of the present invention, an individual will enter a user name and password and then press the submit button. The computer program will then authenticate the user name and password to see if the user name and password are valid. If the user name and password are invalid, the person will not gain access to the computer program. The login page will generally reappear so that another user name and password may be entered. The software program may limit the number of invalid entries before the computer program locks a user out for a predetermined time period.

Figure 4:
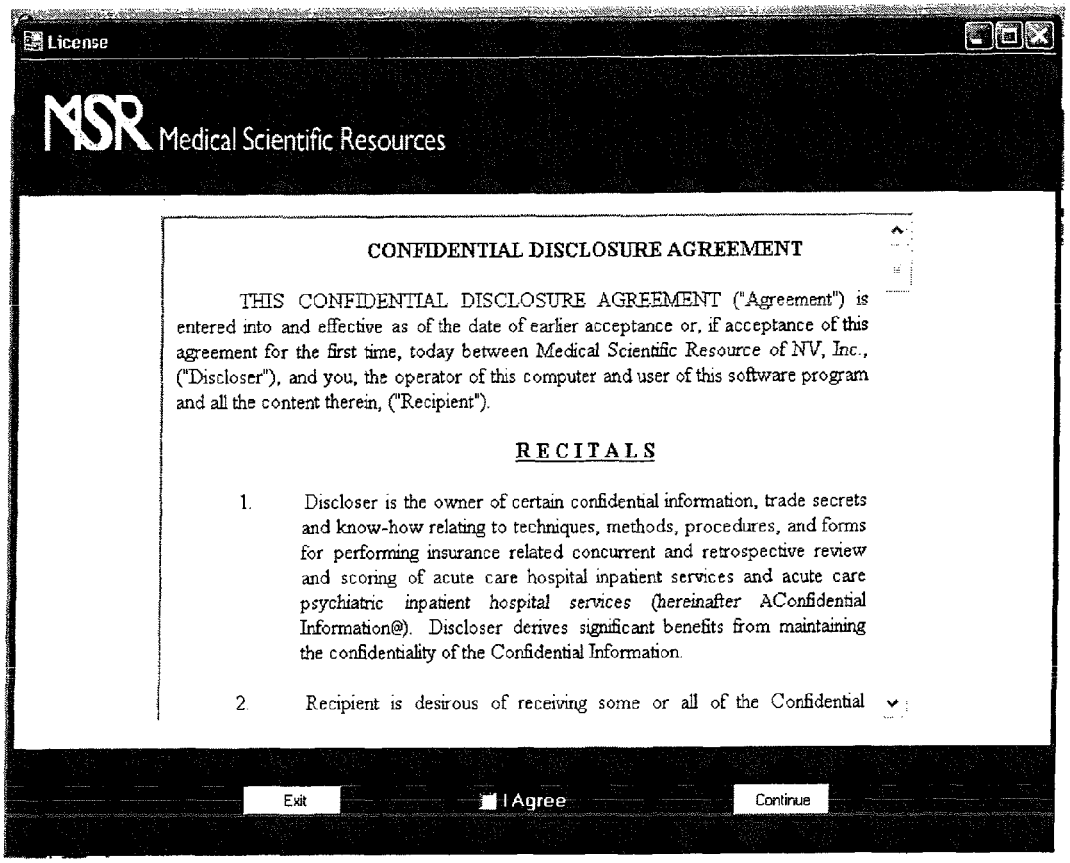
FIG. 4 is the license agreement screen for the software application program.

If the user name and password are valid, the user will then be sent to a confidentiality page as shown in FIG. 4. In order to access the computer program, the user will have to agree to the terms of the Confidential Disclosure Agreement. The user will check the I Agree box and press the Continue button. If the user does not check the I Agree button, the user will not gain access. Once the I Agree box is checked and the Continue button pressed, the user will gain access to the computer program.

Figure 5:
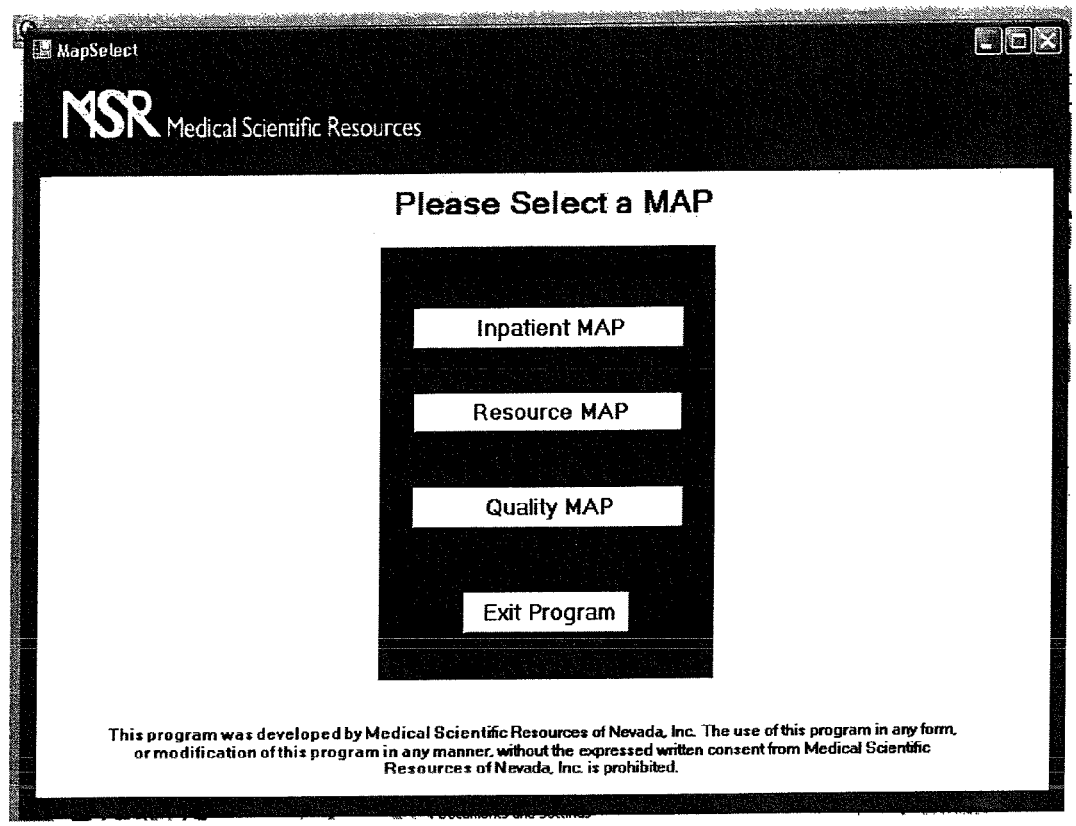
FIG. 5 is the Main Menu screen of the software application program.

Once the I Agree box is checked and the Continue button pressed, the user will be sent to a main page shown in FIG. 5. The main page will show the different modules of the computer program. The user may then select any of the three modules to access. The user may select either inpatient MAP, resource MAP, or quality MAP to view Patient Information Screen. The user may also select the Exit button to exit the computer program.

Figure 2:
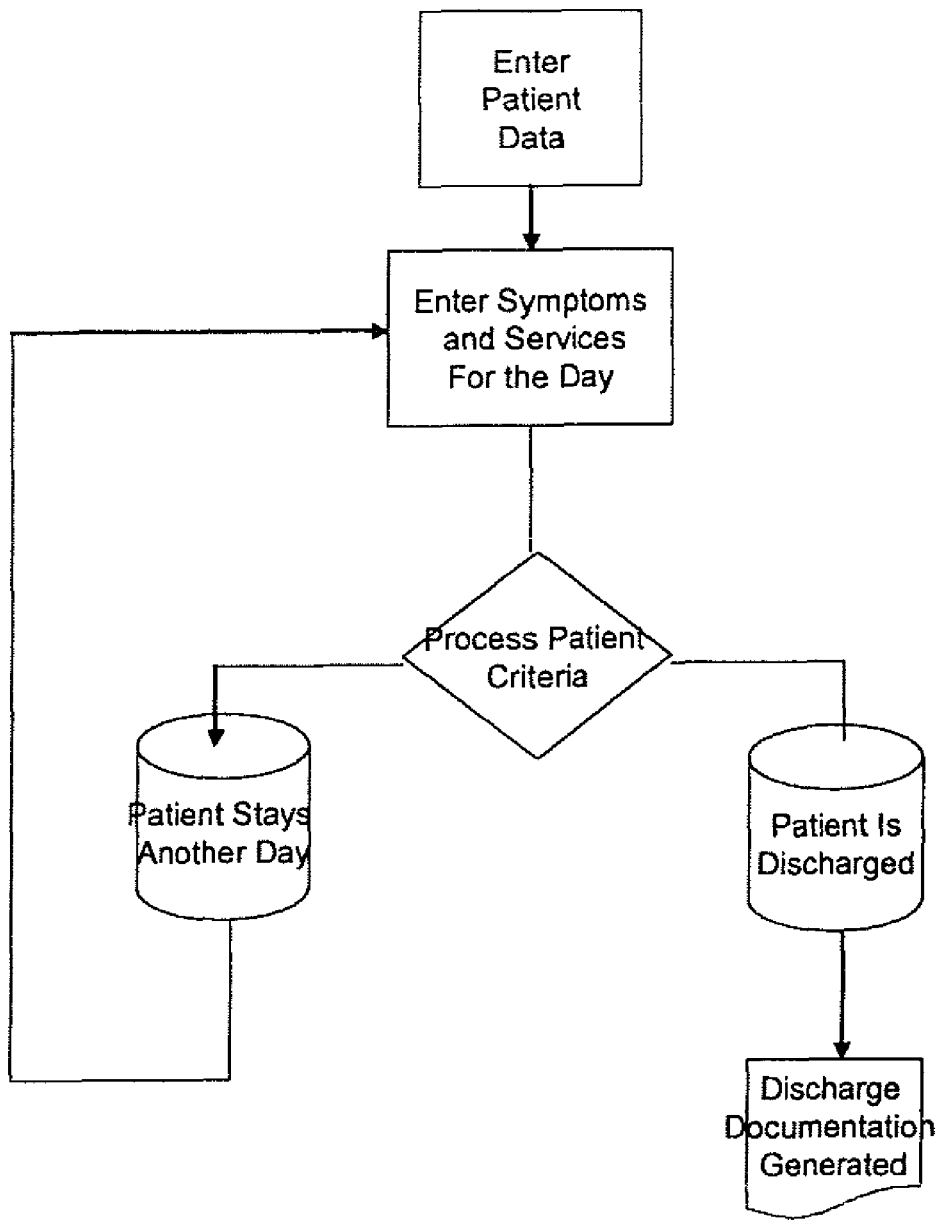
FIG. 2 is a flow diagram of the inpatient MAP module of the software application program.

Referring to FIG. 2, a flow diagram of the inpatient MAP is shown. The MSR Inpatient MAP is used to support hospital discharge or continued stay recommendations. It is a concurrent review instrument completed by a nurse or qualified professional reviewer, on site or telephonic. The MSR Inpatient MAP is a real time system to monitor a hospital patient's need for continued hospitalization or for extended observation. This system employs a series of objective metrics to determine if a patient requires a continued hospital stay. These metrics are pre-programmed into the computer software application. Patient data is entered via computer by a nurse or qualified professional, and consist of the patient's symptoms, treatment, and other services performed. The data is then processed and a determination is displayed recommending whether the patient should be discharged or remain hospitalized. In addition, a record of patient symptoms and services rendered can be transferred to a health data management system providing data for patient care studies and hospital resource allocation.

Figure 6:
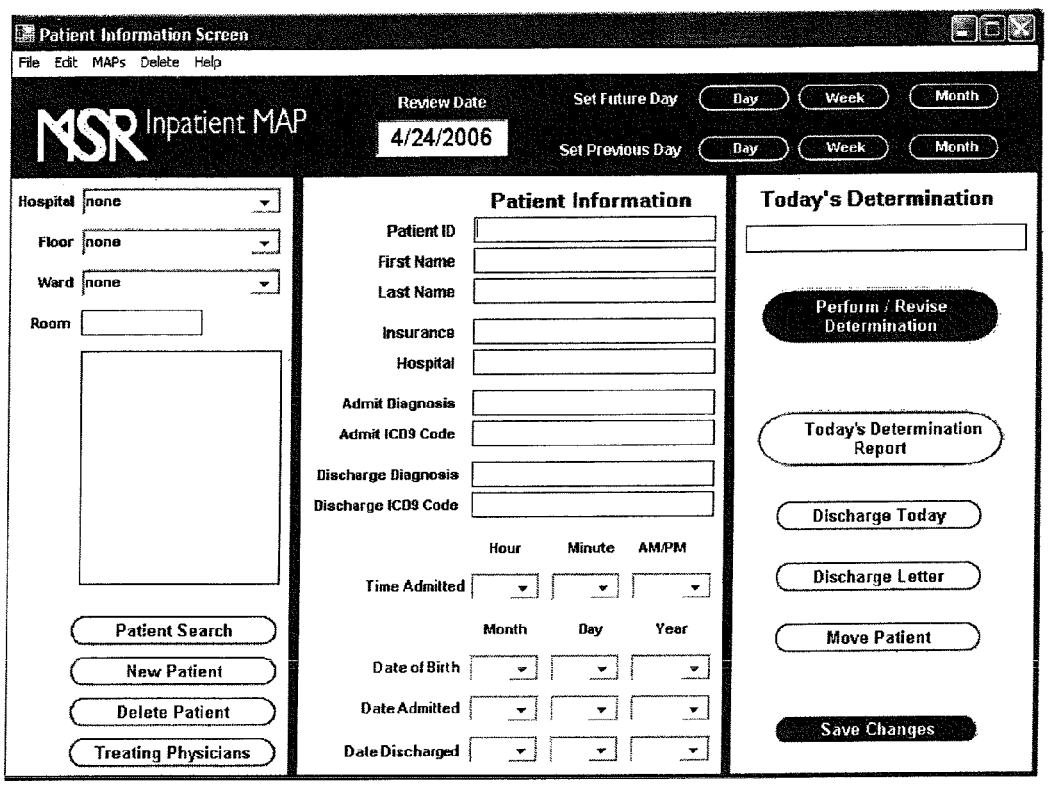
FIG. 6 is the Inpatient Information screen for the software application program.

In general, the Inpatient MAP works in the following manner. A patient's background data is entered into the program database. As seen in FIG. 6, Patient Information screen for the Inpatient MAP is shown. The Patient Information screen is similar to a patient intake form. A person will enter the hospital or facility, floor, ward, and a room number if assigned. A pull down menu may be located to quicken the process of entering the information. To enter a new hospital, floor or ward that is not in the pull-down menu one will press the File menu button and scroll down to New. The new hospital, floor or ward that is not in the pull-down menu is entered in the appropriate location. The Save button in the File pull down menu is then pressed to save the new entry.

Next, information regarding the patent is entered. The patient information will include information such as, but not limited to: Patient ID Number, Patient first and last name, insurance company, hospital, initial diagnosis and code, admit time and date, birthday, etc. As stated above, this listing of patient information is given as an example and should not be seen as to limit the scope of the present invention. Other information may be entered without departing from the spirit and scope of the present invention.

Patient data may be entered in a number of different ways. In accordance with one embodiment of the present invention, to enter a patient a person will enter the desired date in the date field on the Patient Information screen. The person will then select the File menu button and select the correct hospital, floor and ward and then scroll down to New on the File pull down menu. The user will then press the New Patient button and enter the patient information. The Save button is then pressed to save the new patient information.

In accordance with another embodiment of the present invention, to enter a patient a person will enter the desired date in the date field on the Patient Information screen. Then New Patient button on the Patient Information screen is pressed. The patient information is then entered in the corresponding locations (i.e., Patient ID Number, Patient first and last name, insurance company, hospital, initial diagnosis and code, admit time and date, birthday, etc.). The Save Changes button is then pressed to save the information. At any time, whenever patient specific fields appear on the Patient Information Page, patient-specific information can be entered and/or changed.

The treating physician should also be entered for the patient entered. In order to enter attending or additional physicians treating the patient, the user press the Treating Physicians button on the Patient Information Screen. A Treating Physician screen will appear where the physician name and descriptive information may be entered. The user can then press a Save button to save this information to the corresponding patient.

On the Patient Information Screen, a user may be able to retrieve previously entered patients currently hospitalized. In order to do a search, the user will use the pull down menus and select the correct Hospital, Floor, and Ward form the list in each appropriate drop down menu. The user will then set the date to the current date if a current date does not appear in date field on the Patient Information Screen. A list of previously entered patients will then appear on the Patient Information Screen. A user may then select the correct patient and the patient-specific information will appear.

To retrieve a previously entered discharged patient, the user will change the date at top center of the Patient Information Screen to a date the patient was hospitalized. The user will then open the drop down menu and select the appropriate hospital, floor and ward. A list of previously entered patients will appear on the Patient Information Screen. The user can then select the correct patient and the patient-specific information will appear.

To retrieve a patient using a Patient Search function, a user will either: (1) press the Patient Search button on the Patient Information Screen, enter the patient's first and/or last name, then press the Search button. All patients having the entered first and/or last name entered will appear on the Patient Information Screen. The user will then double click on patient name to be retrieved; or (2) a user may press the Patient Search button on the Patient Information Screen. If the user presses the Search button without entering a name, all patient names will appear. The user will then double click on the desired patient name to be retrieved.

The program will allow a user to move a patient to a different hospital or facility, floor, ward or room. In order to move a patient, the user will press the Move Patient button on the Patient Information Screen. The user may then either select (1) to correct location data entered in error; or (2) to move patient to new location and create a new record. In order to correct data entered in error; the user will enter the correct or new location information in the Move Patient Screen and press Save Changes. To delete, change or add patient-specific information, the user will display the patient on the Patient Information Screen. The user will enter the changes or deletions and then press the Save Changes button.

To delete a patient's record, the user will select the desired patient to be deleted. The user will then press the Delete Patient on the Patient Information Screen. The program will confirm if the user wants the selected patient to be deleted in order to prevent accidental deletion of a patient. If the user wants to confirm the deletion of the patient information, the user will then press the Yes button. Alternatively, the user may select the patient to be deleted, press the Delete button in the top bar, select the desired Patient to delete, and then press the Yes button.

A user may also delete a hospital, floor and/or ward and all associated patients associated with the hospital, floor or ward. In order to delete a hospital, floor or ward, the user will press the Delete button on the top bar. The user will then select the desired Hospital, Floor or Ward to delete. The user will press the Yes button to confirm the deletion. Like above, the software program will confirm if the user wants the selected patient to be deleted in order to prevent accidental deletion of a patient.

The computer program may be used to determine if a patient should be discharged or continue to stay at the hospital. Once the patient information is entered, a determination report may be generated. In order to do a determination, the user will open the Patient Information Screen and select a patient for review. Once a patient is selected, the user will enter the date the determination is to be made and press the Perform Determination button. Once the Perform Determination button is pressed, a symptoms and services page is shown.

Figure 7:
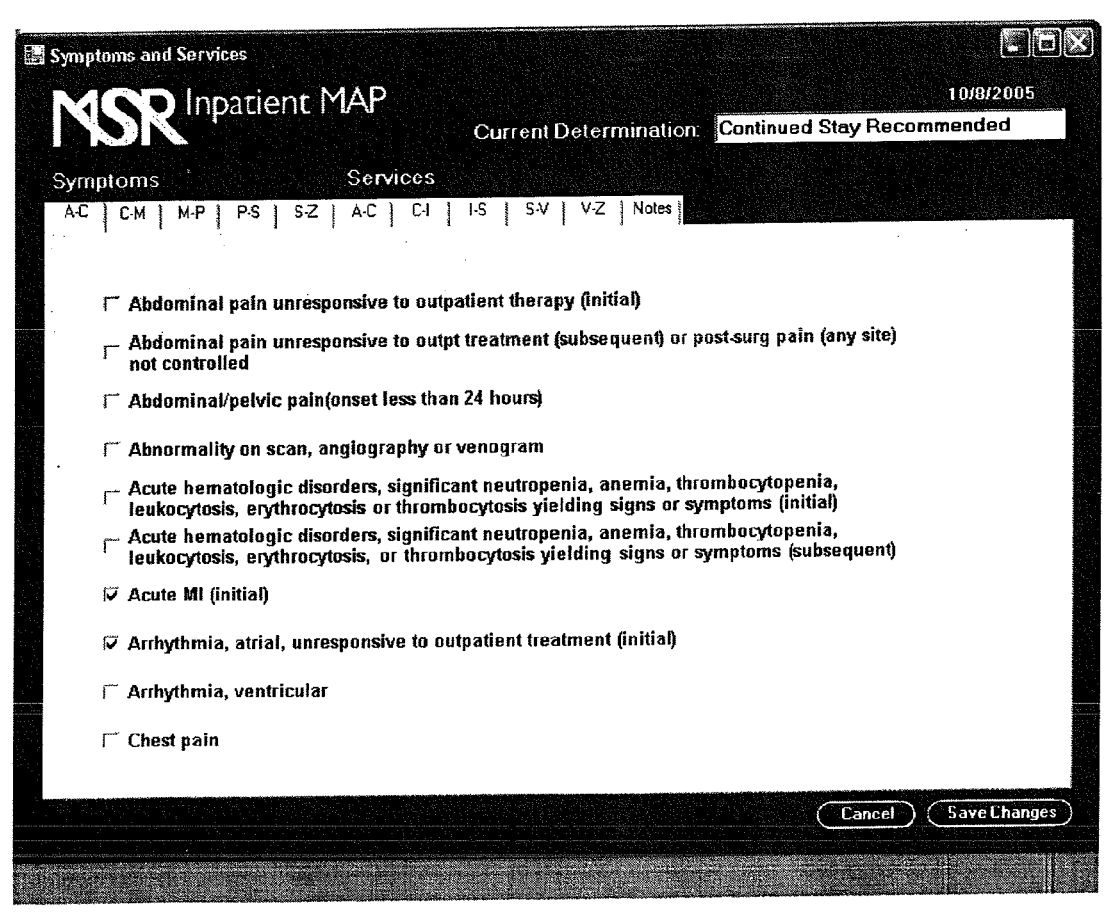

Referring to FIG. 7, one example of a Symptoms and Services screen is shown. The Symptoms and Services screen will list a plurality of different symptoms the patient may be suffering from and/or services the patient may require. In accordance with the embodiment depicted in FIG. 7, the symptoms and services are arranged alphabetically. The symptoms and services are each arranged alphabetically under a plurality of different tabs. In FIG. 7, five tabs are shown for Symptoms and five tabs are shown for Services. There is also one tab for entering notes. The number of tabs shown is given as an example and should not be seen as to limit the scope of the present invention.

Each tab will display a plurality of different symptoms or services for that particular tab heading. In the embodiment depicted in FIG. 7, the A-C tab for symptoms is shown. Thus, symptoms beginning with an A, B or C are listed. Medical personnel using the program will then place a check next to each symptom the patient may be suffering from and service the patient requires for the date of review. When the cursor is placed over a specific symptom and/or service, a definition will appear describing the symptom and/or service. Medical personnel should adhere to the specific definitions which appear when the curser is placed over the symptom and/or service. The Notes tab is used to clarify if the reviewer concludes that continued stay is appropriate even though the review results recommend discharge or if the reviewer wishes to enter additional patient-specific notes.

If a particular symptom and/or service are not listed, the user may enter a custom symptom and/or service in the MSR Resource MAP. The user must first open the Patient Information Screen and then display a patient on Patient Information Screen for review. The user will then press List Resources Used in the menu on the Patient Information Screen to display the Resources and Services tabs. A user may then display a custom row tab (Symptoms S-Z, or Services V-Z, or Other tab) to reveal custom service options available. The user will press Custom Services to display a Custom Services Screen. The user will then enter a custom service including definitions and press the Save button.

Once all the symptom and/or service has been entered and checked, the user will press the Save Changes button. The data entered is then used to make the decision whether the patient should stay in the hospital or be discharged. A recommendation to continue stay or discharge will appear in the on the Patient Information Screen.

In order to perform a determination report, each symptom and service under each tab heading is assigned a specific numeric number. The numeric number will be based on the severity of the symptom/service. For example, each symptom/service will be assigned a numeric value from 0-10. The higher the numeric value, the more severe the symptom/service is. Once the medical personnel using the program has place a check next to each symptom the patient may be suffering from and each service the patient requires, a calculation is performed.

The calculation will add up all the numeric values of all the checked symptoms/services. If the total value of the calculation is equal to or exceeds a predetermined number, a recommendation will be made that the patient should stay in the hospital. For example, in FIG. 7, both Acute MI and Arrhythmia are checked. If Acute MI is given 8 points and Arrhythmia is also given 4 points, then the patient would have a total of 12 points if Acute MI and Arrhythmia are the only symptoms/services checked. If a total of 15 points is required to recommend a stay at the hospital, then the software program will make a recommendation that the patient be discharged. However, if additional symptoms/services are checked, and the total is equal to or greater than 15 points, a recommendation is made for the patient to be admitted/stay another day. If a recommendation to stay is given, the data is stored, and the above steps will be repeated the next day. If a recommendation is made to discharge the patient, the data is saved. A discharge document may be generated ff a recommendation is made to discharge the patient. To generate a discharge document, the user only has to press the Discharge Letter button on the Patient Identification Screen (FIG. 6).

To revise the day's determination in the Inpatient MAP, the user will press the Revise Determination button on the Patient Identification Screen (FIG. 6). The user will then revise the data and press the Save Changes button.

A user may print the Determination Report if desired. To print a Today's Determination Report, a user will press the Today's Determination Report button on the Patient Information Screen (FIG. 6). A template containing the patient's identifying information and the identified symptoms and services appears. Modify the template, and press the print button on the File menu. If need be, the user may need to first attach the computer storing the computer program to a printer and print.

The MSR Quality MAP is another module of the computer software program. The MSR Quality MAP used to obtain real time data for quality improvement projects. The MSR Quality MAP is a data collection instrument completed by a surveyor to monitor daily the quality of the services provided. The MSR Quality MAP quality improvement project findings, when shared with treating physicians and patients, promote objective treatment, continuum of care and quality improvement decisions required by accrediting and certifying organizations.

Figure 9:
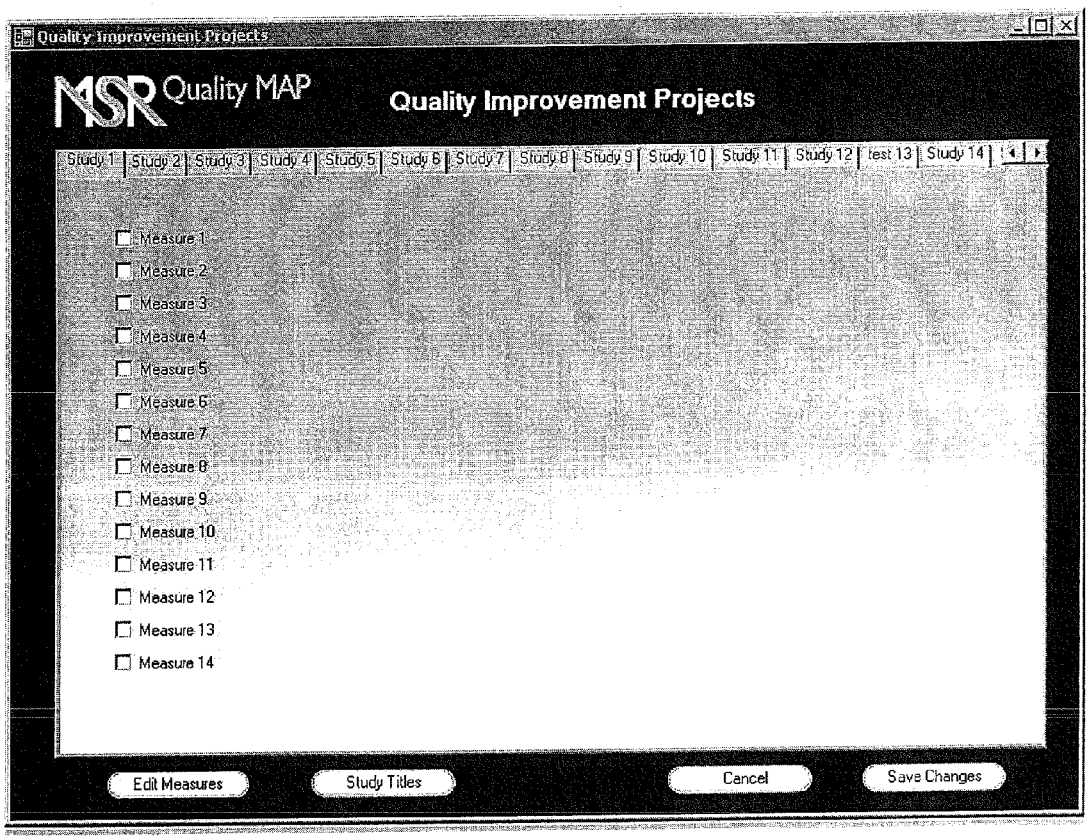
FIG. 9 is a Quality Improvement Project Screen for the Quality MAP module.

The Quality MAP will list a plurality of different conditions/illnesses as shown in FIG. 9. The user will select a particular condition/illness as listed in the tabs and labeled as Study #. Once a desired illness is selected, guidelines will come up showing how to treat the condition/illness. The guidelines will generally be professionally accepted guidelines for treating the condition/illness. When a particular condition/illness is selected, a checklist will come up (i.e., measure checklist). The checklist is to be used to mark what treatment/step has been taken.

Figure 8:
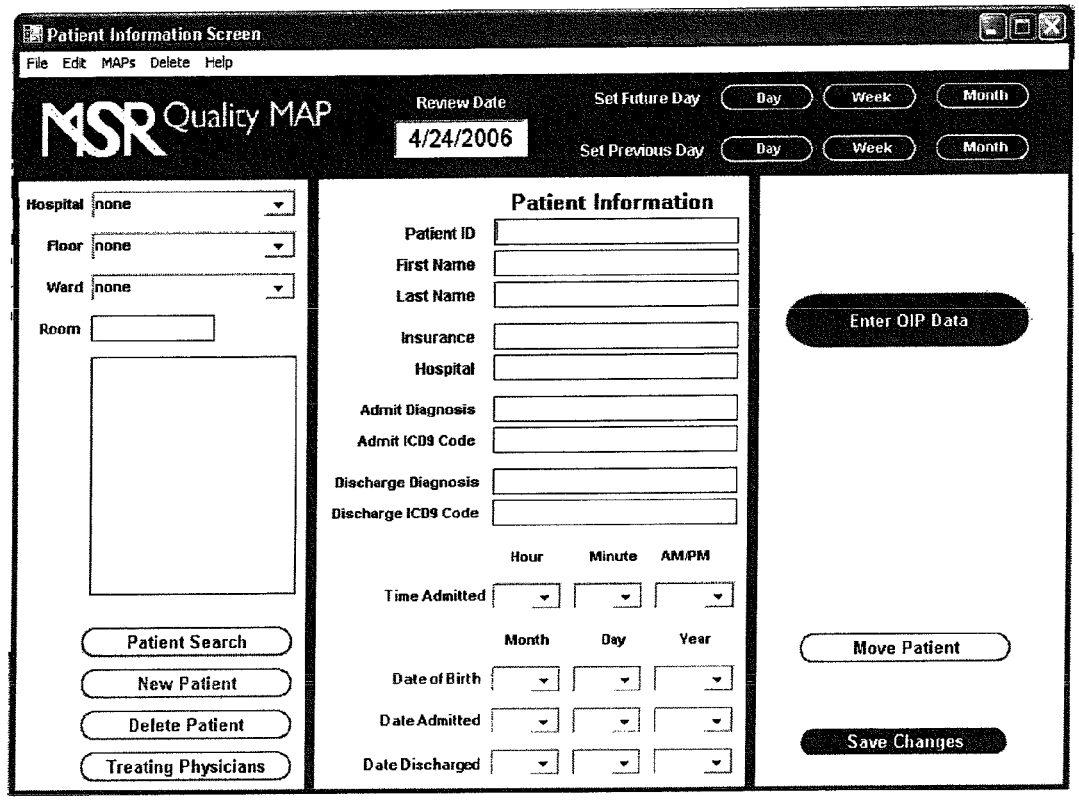
FIG. 8 is the Quality MAP Patient Information screen for the software application program.
Figure 10:
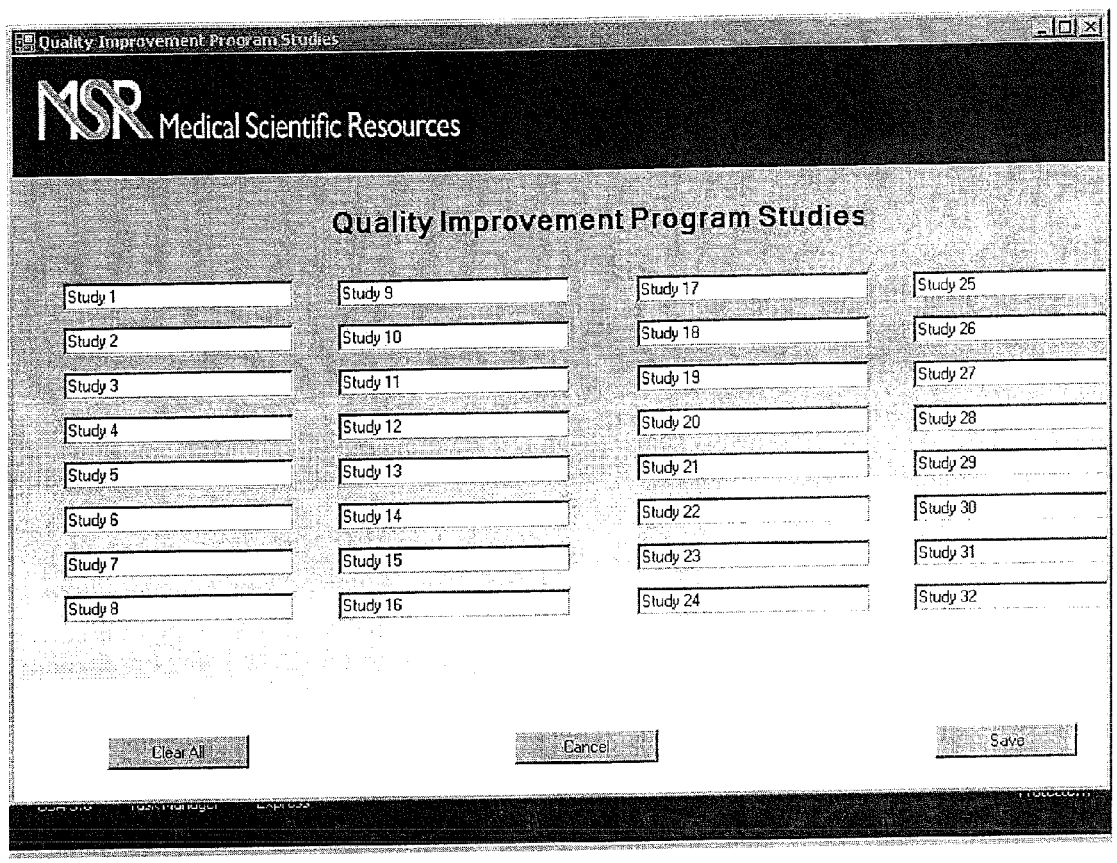
FIG. 10 is a Quality Improvement Program Studies screen for the Quality MAP module.

A user can access the Quality MAP by pressing the Quality MAP button after logging into the system (FIG. 5). This will open up a MSR Quality MAP Screen as shown in FIG. 8. To title a QIP (Quality Improvement Program-Study) in the MSR Quality MAP screen, the user will select a patient. The user will then press the Enter QIP Data button. The user will be sent to an MSR Quality MAP QIP screen as shown in FIG. 9. The user will press the Study Titles button which will send the user to an MSR QIP Studies screen (FIG. 10). The user will enter a study title and then press the Save button. The user will be sent back to the Quality MAP QIP screen (FIG. 9) where the user will then press the Save Changes button.

Figure 11:
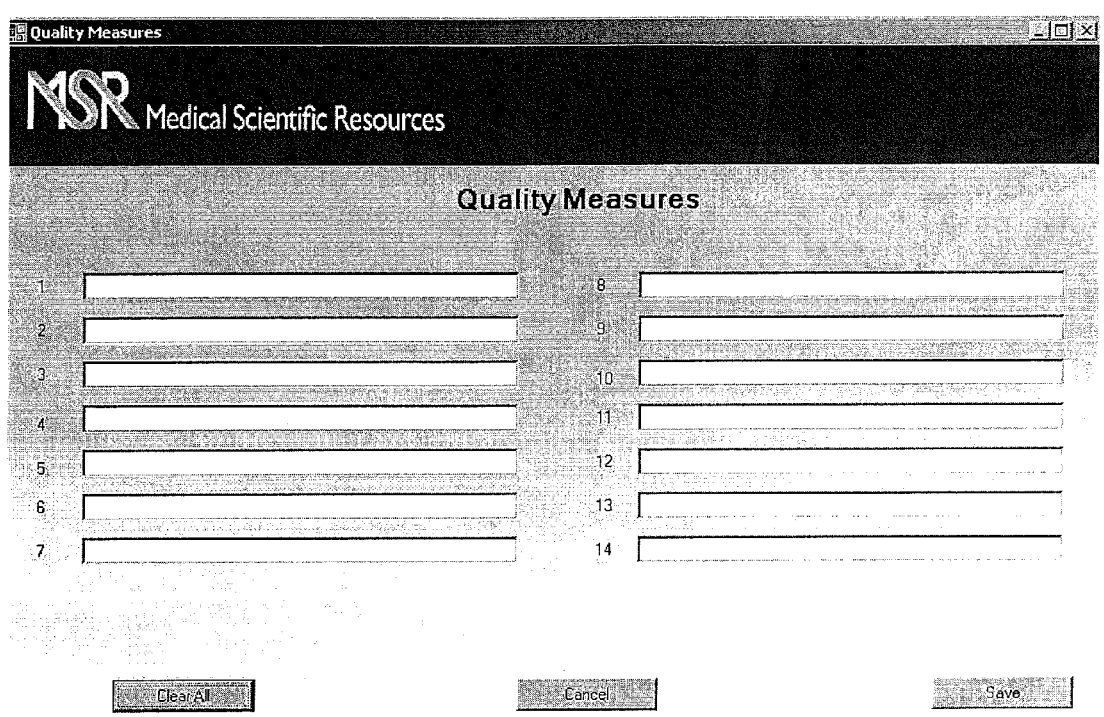
FIG. 11 is a Quality Measures screen for the Quality MAP module.

To enter a QIP measures for a study in the MSR Quality MAP screen, the user will open the MSR Quality MAP Patient Information Screen (FIG. 8) and select a patient. The user will then press the Enter QIP Data button. The user will be sent to an MSR Quality MAP QIP screen (FIG. 9). The user will select a specific Study Title listed in the menu tab (i.e., Study 1-Study XX). It should be noted that while fourteen studies are shown, the user may press on the arrow key to show additional Study Titles. Once a specific Study Title is selected, the user will press the Edit Measures button. The user will be sent to a MSR Quality Measures screen as shown in FIG. 11. The user will then enter Quality Measures, press the Save button on the MSR Quality Measures screen, then press the Save Changes button on the Quality Improvement Screen.

To enter a patient Quality Improvement Project data, a user will open the MSR Quality MAP Patient Information Screen (shown in FIG. 8. The user will then select a desired patient. The user will press the Enter QIP Data button and then press a specific Study Title for review. The user will place a check in the box(s) next to the measure(s) completed and then press the Save Changes. Thus, a user can keep tract of all measures used to treat the patient.

Thus, the Quality MAP has several functions. First, the Quality MAP will list a plurality of different conditions/illnesses and show the guidelines for treating the condition/illness. The guidelines will generally be government recommended guidelines for treating the condition/illness. The Quality MAP will further keep a detailed list of the measures used to treat the patient.

The MSR Resource MAP is another module of the computer software program. The MSR Resource MAP is used to determine effective allocation of hospital staff and other resources. The MSR Resource MAP is completed by a surveyor. It is specifically designed for the daily review of hospital units and hospitalized patients to measure resources consumed. The data entered into the MSR Resource MAP can be downloaded into enterprise systems for analysis.

Figure 12:
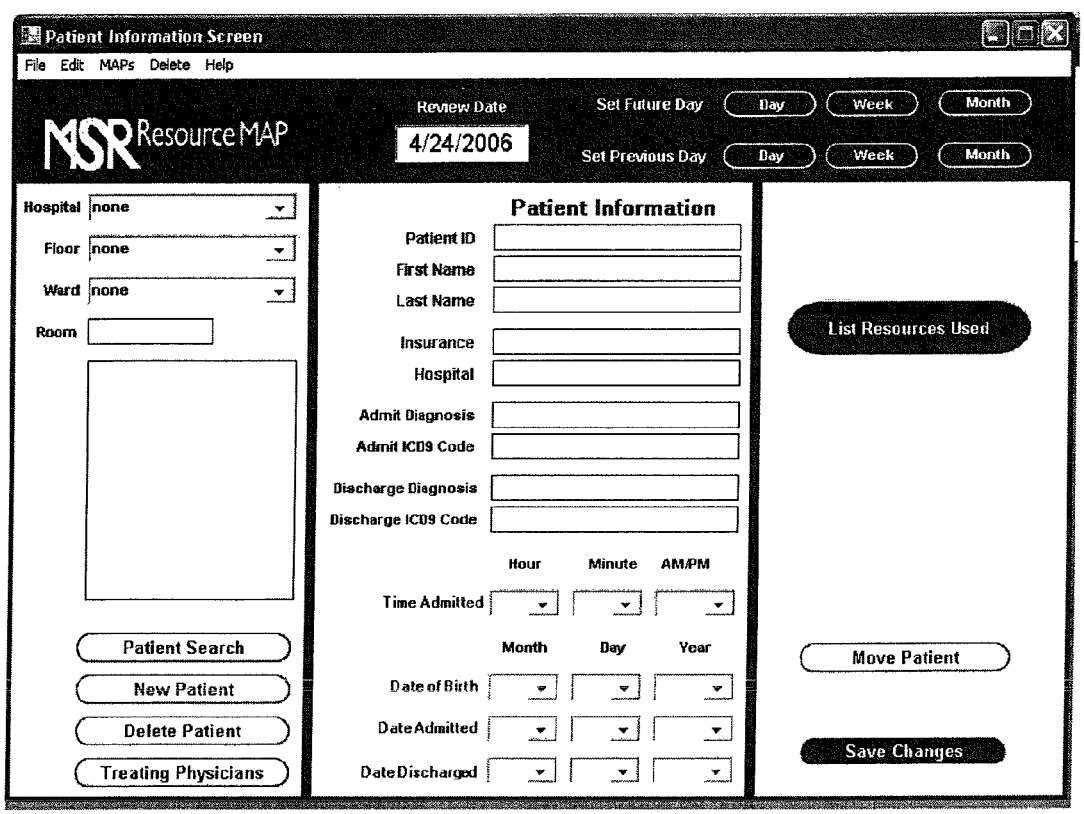
FIG. 12 is the Resource MAP Patient Information screen for the software application program.
Figure 13:
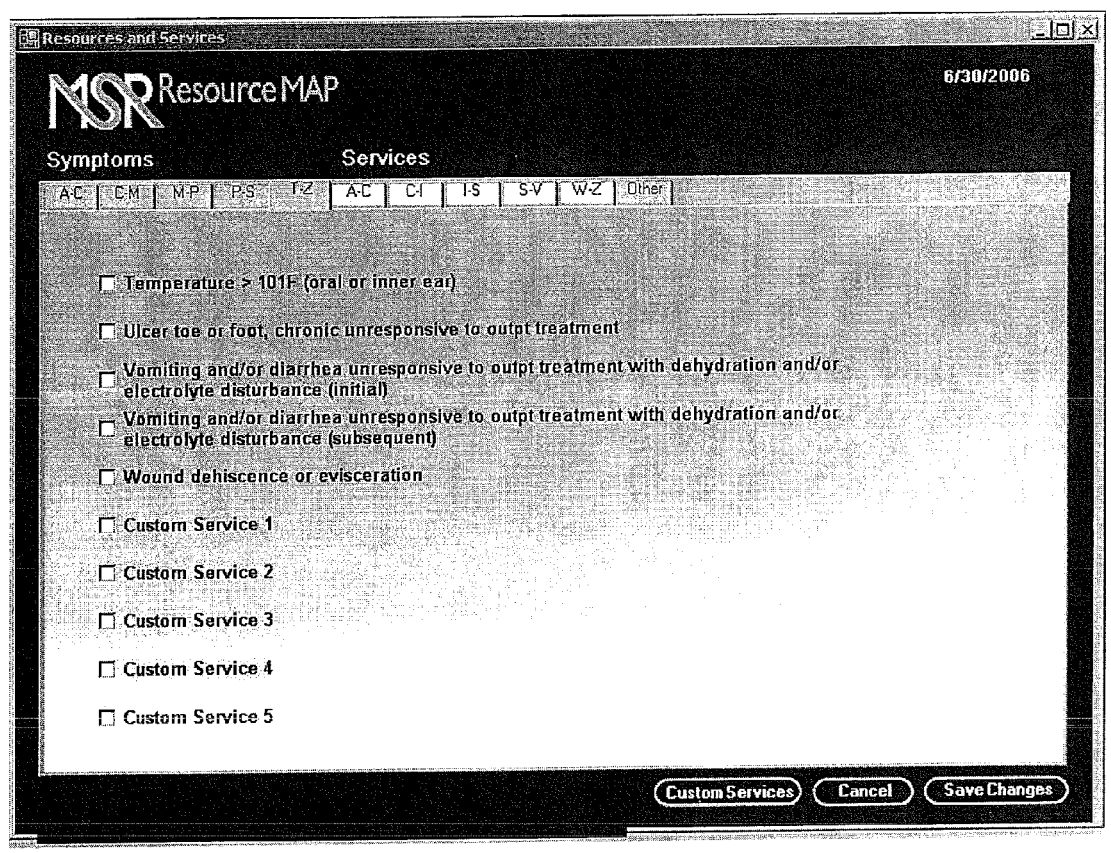
FIG. 13 is a Resource MAP Symptoms/Services screen for the software application program.
Figure 14:
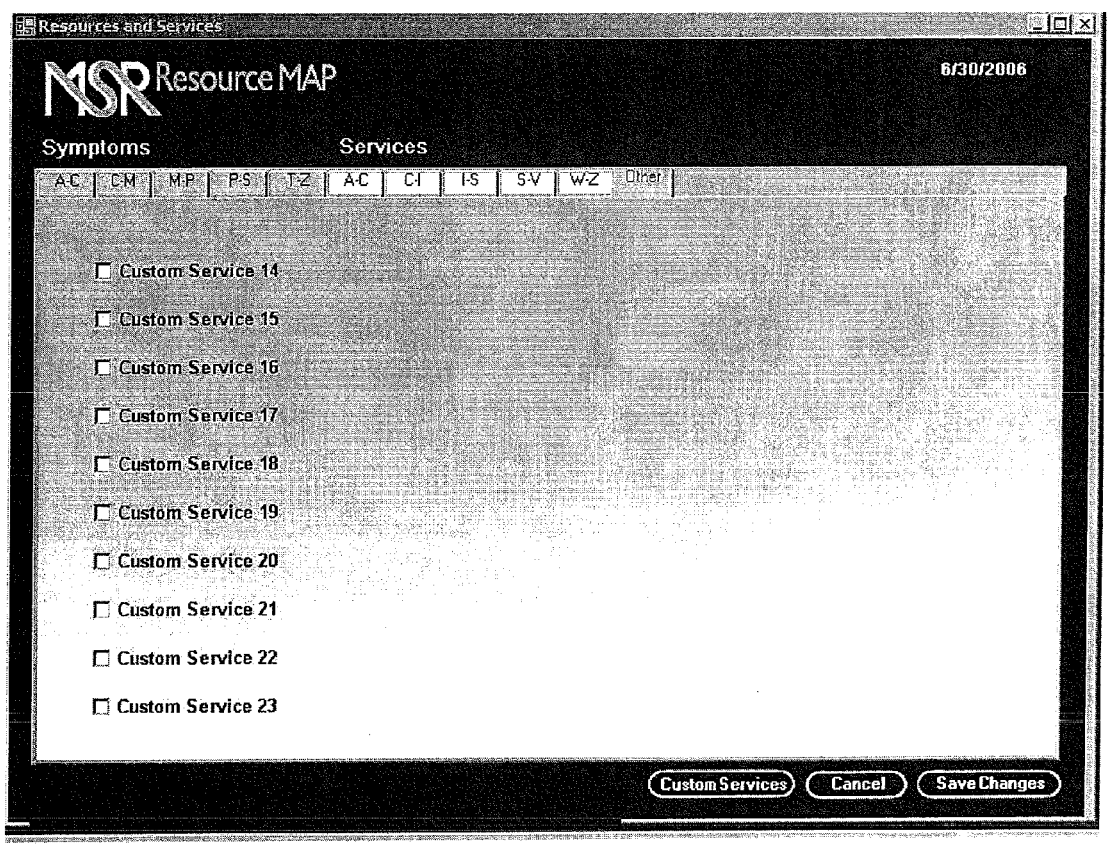
FIG. 14 is a custom Resource MAP Symptoms/Services screen for the software application program.

To perform an MSR Resource MAP review, the user will press the Resource MAP button after logging into the system (FIG. 5). This will open up a Resource MAP Patient Information Screen as shown in FIG. 12. The user will select a patient for review. The user will display the date the determination is to be made on the Patient Information Screen and then press the List Resources Used button. The Symptoms and Services Screen as shown in FIG. 13 appears revealing a plurality of Symptoms tabs, a plurality of Services tabs and an Other tab. Each Symptoms and Services tab contains a list of preprogrammed alphabetized options. In addition, custom services specifically included for review are found in the last Symptoms tab, the last Services tab and/or the Other tab. A user will place a check only in the box next to the symptoms and/or services which apply to the patient on the date of review. The user should adhere to the specific definitions which appear when the curser is placed over the symptom or service, or are noted in the custom services lines. After all applicable fields are checked press Save Changes.

To revise a MSR Resource MAP determination, a user will open the Resource MAP Patient Information Screen and select the date the revised determination is to be made. The user will then select a patient for review. The user will press the List Resources Used button, revise determination and the press Save Changes.

Thus, the MSR Resource MAP one can monitor the resources consumed by all patients for a particular hospital, floor, ward, etc. By reviewing the data, one can determine if a particular hospital, floor, ward as sufficient supplies, staffing, etc. Once can further monitor if the staff is adequately caring for the patients in a particular hospital, floor, ward, etc.

This disclosure provides exemplary embodiments of the present invention. The scope of the present invention is not limited by these exemplary embodiments. Numerous variations, whether explicitly provided for by the specification or implied by the specification, such as variations in structure, dimension, type of material and manufacturing process may be implemented by one of skill in the art in view of this disclosure.

What is claimed is:

1. A computer system comprising a processor for executing program instructions and a memory coupled to the processor for storing the program instructions, the programming instructions comprising:
   enter intake data on a patient; entering symptoms the patient is experiencing and services performed on the patient, wherein all symptom and services listed in the program instructions are assigned a numeric value based on severity of the symptom and service;
   calculating total of all numeric values of symptoms patient is experiencing and services performed on the patient;
   determining if a payer of services for the patient will approve payment based on total of all numeric values of symptoms patient is experiencing and total of all numeric values of services performed or to be performed on the patient;
   making a recommendation to one of admit, continued hospital stay or discharge of the patient based on total numeric value of symptoms patient is experiencing and total numeric value of services performed on the patient, wherein total numeric value of symptoms patient is experiencing and total numeric value of services performed on the patient is based on if a payer of services for the patient will approve payment; and
   wherein making a recommendation further comprises recommending extending hospital stay if the total value of all total numeric values is one of equal to or exceeds a predetermined number.

2. A computer system in accordance with claim 1, wherein making a recommendation further comprises recommending discharge from the hospital if the total value of all numeric values is less than the predetermined number.

3. A computer system in accordance with claim 2, wherein making a recommendation further comprises generating a discharge document if the total value of all numeric values is less than the predetermined number.

4. A computer system in accordance with claim 1, wherein the programming instructions further comprises entering a user name and password to prevent unauthorized users from entering and/or reviewing data stored in the programming instructions.

5. A computer system in accordance with claim 1, wherein the programming instructions further comprises entering search data to locate a patient.

6. A computer system in accordance with claim 5, wherein entering search data to locate a patient further comprises entering at least one of hospital, floor, ward, patient ID, first name, and last name.

7. A computer system in accordance with claim 1, wherein the programming instructions further comprises entering at least one of a custom symptom or custom service listed in the program instructions when one of a symptom or service is not listed in the program instructions.

8. A computer system in accordance with claim 1, wherein the programming instructions further comprises providing a notes section to input information to clarify at least one of a symptom or service.

9. A computer system in accordance with claim 1, wherein the programming instructions further comprises updating patient data to change location of patient from at least one of changing a hospital or facility, floor, ward or room.

10. A computer system in accordance with claim 1, wherein the programming instructions further comprises providing a quality MAP, the quality MAP is a data collection instrument to monitor daily the quality of the services provided.

11. A computer system in accordance with claim 10, wherein providing the quality MAP further comprises listing a plurality of different conditions/illnesses, wherein guidelines will show how to treat a selected condition/illness.

12. A computer system in accordance with claim 11, wherein the guidelines showing how to treat a selected condition/illness are professionally accepted guidelines.

13. A computer system in accordance with claim 10, wherein the quality MAP further comprises providing inputs for indicating that a particular measure has been taken to treat the selected condition/illness.

14. A computer system in accordance with claim 1, wherein the programming instructions further comprises providing a resource MAP to determine effective allocation of hospital staff and other resources.

15. A computer system in accordance with claim 14, wherein the providing a resource MAP to determine effective allocation of hospital staff and other resources further comprises:
   monitoring resources consumed by all patients for one of a particular hospital, floor, and ward; and
   reviewing data to determine if one of the hospital, floor, ward has sufficient supplies and staffing.

16. A computer system comprising a processor for executing program instructions and a memory coupled to the processor for storing the program instructions, the programming instructions comprising:
   enter intake data on a patient;
   entering symptoms the patient is experiencing and services performed on the patient, wherein all symptom and services listed in the program instructions are assigned a numeric value based on severity of the symptom and service;
   calculating total of all numeric values of symptoms patient is experiencing and services performed on the patient;
   determining if a payer of services for the patient will approve payment based on total of all numeric values of symptoms patient is experiencing and services performed or to be performed on the patient;
   making a recommendation to one of admit, continued hospital stay or discharge of the patient based on if the payer of services for the patient will approve payment based on total of all numeric values of symptoms patient is experiencing and services performed or to be performed on the patient;

listing a plurality of different conditions/illnesses;

displaying guidelines to show how to treat a selected condition/illness;

entering marks for indicating that a particular measure has been taken to treat the selected condition/illness;

monitoring resources consumed by all patients for one of a particular hospital, floor, and ward;

reviewing data to determine if one of the hospital, floor, ward has sufficient supplies and staffing; and preparing a report of patient information, symptoms and services rendered to determine if proper procedures were followed and to verify payment for services.

17. A computer system in accordance with claim 16 recommending one of extending hospital stay if the total value of all numeric values is one of equal to or exceeds a predetermined number or discharge from the hospital if the total value of all numeric values is less than the predetermined number.

18. A computer system in accordance with claim 17, wherein recommending one of extending or discharging further comprises generating a discharge document if the total value of all numeric values is one of equal to or exceeds a predetermined number.

19. A computer system in accordance with claim 16, wherein the programming instructions further comprises updating patient data to change location of patient from at least one of changing a hospital or facility, floor, ward or room.

* * * * *